United States Patent
Newman et al.

(10) Patent No.: US 6,494,833 B1
(45) Date of Patent: Dec. 17, 2002

(54) CONDITIONING APPARATUS FOR A CHEMICAL SENSING INSTRUMENT

(75) Inventors: Richard W. Newman, Auburn, NY (US); Dominick A. Danna, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 43 days.

(21) Appl. No.: 09/884,391

(22) Filed: Jun. 19, 2001

(51) Int. Cl.[7] .................................................. A61B 5/00
(52) U.S. Cl. ...................................... 600/309; 600/345
(58) Field of Search ........................ 600/309, 345–349, 600/352–361, 365, 573, 576, 578, 579, 583; 606/181–183

(56) References Cited

U.S. PATENT DOCUMENTS

| | | |
|---|---|---|
| 4,010,738 A | 3/1977 | Preti et al. |
| 4,218,298 A | 8/1980 | Shimada et al. |
| 4,595,011 A | 6/1986 | Phillips |
| 4,821,732 A | 4/1989 | Lippes |
| 4,887,455 A | 12/1989 | Payne et al. |
| 4,992,244 A | 2/1991 | Grate |
| 5,094,955 A | 3/1992 | Calandra et al. |
| 5,098,830 A | 3/1992 | Bar-or et al. |
| 5,120,421 A | 6/1992 | Glass et al. |
| 5,164,796 A | 11/1992 | Di Guiseppi et al. |
| 5,571,401 A | 11/1996 | Lewis et al. |
| 5,674,752 A | 10/1997 | Buckley et al. |
| 5,675,070 A | 10/1997 | Gelperin |
| 5,698,089 A | 12/1997 | Lewis et al. |
| 5,788,833 A | 8/1998 | Lewis et al. |
| 5,799,102 A | 8/1998 | Leong |
| 5,807,701 A | 9/1998 | Payne et al. |
| 5,882,497 A | 3/1999 | Persaud et al. |
| 5,891,398 A | 4/1999 | Lewis et al. |
| 5,911,872 A | 6/1999 | Lewis et al. |
| 5,919,143 A | 7/1999 | Jenkins et al. |
| 5,951,486 A | 9/1999 | Jenkins et al. |
| 5,951,846 A | 9/1999 | Lewis et al. |
| 5,959,191 A | 9/1999 | Lewis et al. |
| 6,013,229 A | 1/2000 | Lewis et al. |
| 6,033,601 A | 3/2000 | Persaud et al. |
| 6,085,576 A | 7/2000 | Sunshine et al. |
| 6,093,308 A | 7/2000 | Lewis et al. |
| 6,234,006 B1 | 5/2001 | Sunshine et al. |
| 6,349,229 B1 * | 2/2002 | Watanabe et al. ........... 600/309 |

FOREIGN PATENT DOCUMENTS

| | | |
|---|---|---|
| WO | 94/04916 | 3/1994 |
| WO | 94/07407 | 4/1994 |

(List continued on next page.)

OTHER PUBLICATIONS

"Sensors and Actuators B, 18–19", *A brief history of electronic noses* pp 211–220 (1994).

(List continued on next page.)

*Primary Examiner*—Tu Ba Hoang
(74) *Attorney, Agent, or Firm*—Wall Marjama & Bilinski LLP

(57) ABSTRACT

A conditioning sleeve for a medical or an industrial diagnostic sensing instrument, in which the instrument has a support for supporting at least one chemical sensing element capable of detecting at least one chemical component of a fluid and producing an electrical signal when said at least one chemical component is detected. The sleeve includes an interior sized for enclosing at least a portion of the support including the at least one chemical sensing element and for producing environmental conditions within the sleeve interior which approximate those of an intended target area. Preferably, at least one heater or cooler and a humidifier approximate the environmental conditions of the target area in order to acclimate the sensing elements of the diagnostic instrument prior to actual use.

16 Claims, 4 Drawing Sheets

FOREIGN PATENT DOCUMENTS

| WO | 96/00384 | 1/1996 |
| WO | 99/09407 | 2/1999 |
| WO | 99/09408 | 2/1999 |
| WO | 99/47905 | 9/1999 |
| WO | 99/66304 | 12/1999 |

OTHER PUBLICATIONS

"Sensors and Actuators B, 4", Gardner et al. *Detection of Vapours and Odours from a Multisensor Array Using Pattern Recognition Part 1. Principal Component and Cluster Analysis*, pp 109–115 (1991).

"Sensors and Actuators B, 18–19", Gardner *A Multisensor System for Beer Flavour Monitoring Using an Array of Conducting Polymers and Predictive Classifiers*, pp 240–243 (1994).

Sensors and Actuators 6, Zaromb et al. *Theoretical Basis For Identification and Measurement of Air Contaminants Using An Array of Sensors Having Partly Overlapping Selectivities*, pp225–243.

"Sensors and Actuators, A21–23" *Electrochemcial Deposition of Conducting Polymers onto Electronic Substratees for Sensor Applications*, pp 911–914 (1990).

Dept. of Engineering, University of Warwick, Coventry, England *Bacteria Detection and Classification Using Artifical Neural Networks in Conjunction with an Electronic Nose*, pp 226–234.

* cited by examiner

CONDITIONING APPARATUS FOR A CHEMICAL SENSING INSTRUMENT

FIELD OF THE INVENTION

The invention relates to the field of diagnostic fluid or vapor measurement and more particularly to a sleeve for conditioning a medical or industrial diagnostic chemical sensing instrument prior to use of the instrument.

BACKGROUND OF THE INVENTION

Chemical sensing devices are commonly known for detecting the presence of certain vapors, such as carbon monoxide and/or carbon dioxide, in either an industrial or home environment. Likewise, further applications of chemical sensing technology are found in the food processing industry.

To date, there are very few known chemical sensing devices which are utilized for medical applications or purposes. In addition most known devices of this type, regardless of the field of use, require a housing which retains at least one chemical sensor. These devices further include means, such as a pump or other similar device, for inputting a portion of the atmosphere of an intended target area into the housing for evaluation by the chemical sensor(s). Such devices are described, for example, in U.S. Pat. No. 5,799,102 to Leong which determines the authenticity of a bank note, and U.S. Pat. No. 5,675,070 to Gelperin in which an array of gas sensors are disposed in an interior testing chamber. The gas sensors of the array can detect the levels of specified gases in a gas mixture and then produce a sensor pattern which can subsequently be analyzed.

Among the problems encountered in using known electronic sensors, such as polymer gas sensors, as described by U.S. Pat. No. 5,571,401 to Lewis et al, U.S. Pat. No. 5,882,497 to Persaud et al, U.S. Pat. No. 6,033,601 to Persaud et al, U.S. Pat. No. 6,013,229 to Lewis, and U.S. Pat. No. 6,093,308, to Lewis, among others, are those relating to stability. Utilizing these sensors in a medical environment; for example, to identify specific vapors indicative of a disease process by exposing the sensors to the interior of the mouth of a patient, could require that the sensors will be subjected to exposure of large changes in both temperature and humidity, as compared to those present in an ambient environment. Therefore and with present sensor technology, substantial and undesirable equalization time periods would be required.

SUMMARY OF THE INVENTION

A primary object of the present invention is to overcome the above noted deficiencies of the prior art.

Another primary object of the present invention is to provide a diagnostic testing or detecting device which can be environmentally calibrated prior to insertion into a target atmosphere in order to suitably and efficiently acclimate the device.

Therefore and according to a preferred aspect of the present invention, there is described a conditioning apparatus for a diagnostic instrument, said instrument comprising a support having at least one chemical sensing element capable of detecting at least one chemical component of a fluid and producing an electrical signal when said at least one chemical component is detected, said conditioning apparatus including:

a sleeve sized for enclosing at least a portion of said support including said at least one chemical sensing element; and means for producing environmental conditions within said sleeve which approximate those of an intended target to be used by said diagnostic instrument.

Preferably, the sleeve includes at least one heating element which selectively heats or cools the interior of the sleeve to a predetermined temperature and/or a humidification chamber to pre-expose the chemical sensing element(s) to an environment approximately equivalent to that of the target atmosphere, such as the interior of the mouth or other suitable medical or industrial target.

According to another preferred aspect of the invention, a method is described for conditioning a diagnostic instrument, the instrument comprising a support for supporting at least one chemical sensing element capable of detecting at least one chemical component of a fluid, said method comprising the steps of:

placing a portion of said support including said at least one chemical sensing element into the interior of a sleeve;

conditioning said at least one chemical sensing element by providing an environment within the interior of said sleeve approximating that of a target;

removing said support from said sleeve; and immediately positioning said support including said at least one chemical sensing element at the target.

Preferably, the target can be a medical and/or an industrial target.

An advantage of the present invention is that the environmental conditions of a target atmosphere can be applied to a chemical sensing element array prior to insertion therein, increasing the efficiency and also improving the reliability of the device.

A further advantage of the present invention is that a conditioning sleeve as described by the present invention can easily be attached and removed from a diagnostic sensing device which includes at least one chemical sensing element capable of detecting at least one chemical component of a fluid or fluids.

These and other objects, features, and advantages will be readily apparent form the following Detailed Description which should be read in conjunction with the accompanying drawings.

DETAILED DESCRIPTION

The following description relates to a preferred diagnostic chemical sensing apparatus having an environmental conditioning sleeve made in accordance with certain preferred embodiments. For purposes of the discussion which follows, "fluid" is defined as anyone of a liquid, gas or vapor. The description further includes a related method of pre-exposing at least one or a plurality of chemical sensing elements of the chemical sensing apparatus to environmental conditions replicating those of a target environment, in which the target environment, such as an anatomical body cavity, e.g., the mouth of a patient, has environmental conditions that are considerably different than those found in ambient surroundings. It should be readily apparent, however, that other modifications and variations are possible within the spirit and scope of the inventive concepts described herein. In addition, certain terms are used throughout this discussion, such as "inner", "outer", "top", "bottom", "distal", "proximal", and the like which are used to provide a frame of reference with regard to the accompanying drawings. These terms, however, are not intended to be limiting of the present invention.

Figure 1:
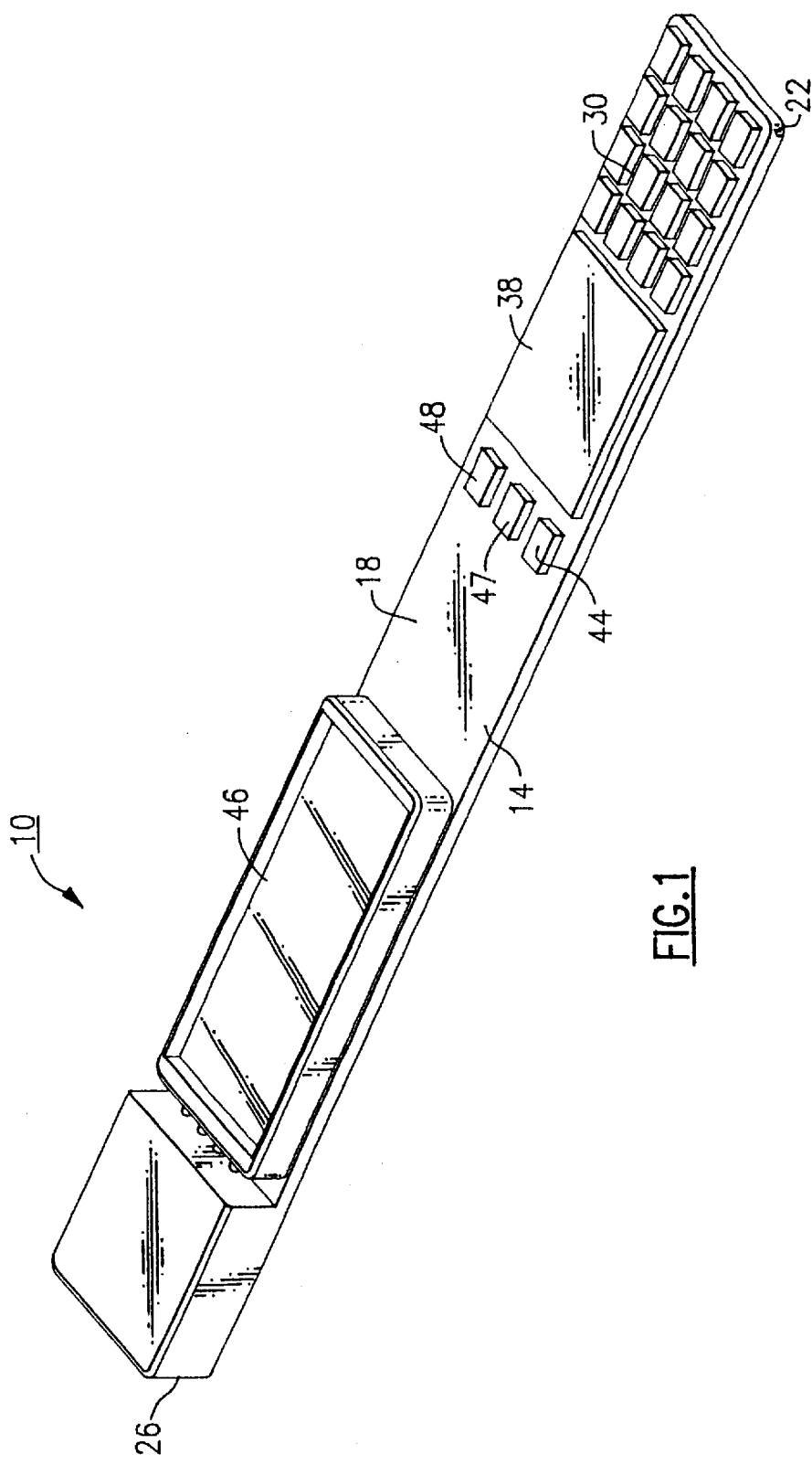
FIG. 1 is a top perspective view of a diagnostic device including a plurality of electronic fluid sensing elements.

Referring to FIG. 1, there is first depicted a diagnostic chemical sensing device 10 comprising an elongated substantially planar substrate 14, made from any suitable biocompatible material such as composite, wood, ceramic or plastic, among others. The elongated substrate 14 according to the present embodiment has a shape and size which closely resembles that of a tongue depressor, for a specific application/use in conjunction with the mouth of a patient (not shown). Other shapes or geometries, however, can easily be imagined.

The elongated substrate 14 includes an exterior surface 18 as well as opposing distal and proximal ends 22, 26, respectively. A plurality or array 30 of chemical sensing elements are disposed on the exterior surface 18 of the elongated substrate 14 in the vicinity of the distal end 22. According to the present embodiment, the chemical sensing elements of the array 30 are miniature polymer gas sensors, such as those manufactured by Cyrano Sciences, Inc. of Pasadena, Calif. or as described in U.S. Pat. No. 5,571,401 to Lewis et al, U.S. Pat. No. 5,882,497 to Persaud et al, U.S. Pat. No. 6,033,601 to Persuad et al, U.S. Pat. No. 6,013,229 to Lewis, and U.S. Pat. No. 6,093,308, to Lewis, the entire contents of each which are herein incorporated by reference. It will be readily apparent, however, that other known chemical sensing elements such as organic gas sensors, conductive composites, metal oxide field effect transistors, surface acoustic wave (SAW) sensors, piezoelectric sensors, catalytic gas sensors, quartz microbalance sensors, and others, can easily be substituted. Each of the sensing elements of the array 30 are capable of detecting a specific fluid, (e.g. gas, liquid or vapor), the presence of which produces an electrical change. The electrical change can be resistance, capacitance, transconductance, conductance, voltage, impedance, resonant frequency, or other perceivable electrical change.

The chemical sensing elements of the array 30 are attached e.g., by epoxy, glass frit, adhesive, or other means to the substrate 14. Alternately, the sensing element array 30 can be provided as part of a plug-in electrical module (not shown) having connectors (not shown) at the distal end 22 of the elongated substrate 14.

Figure 2:
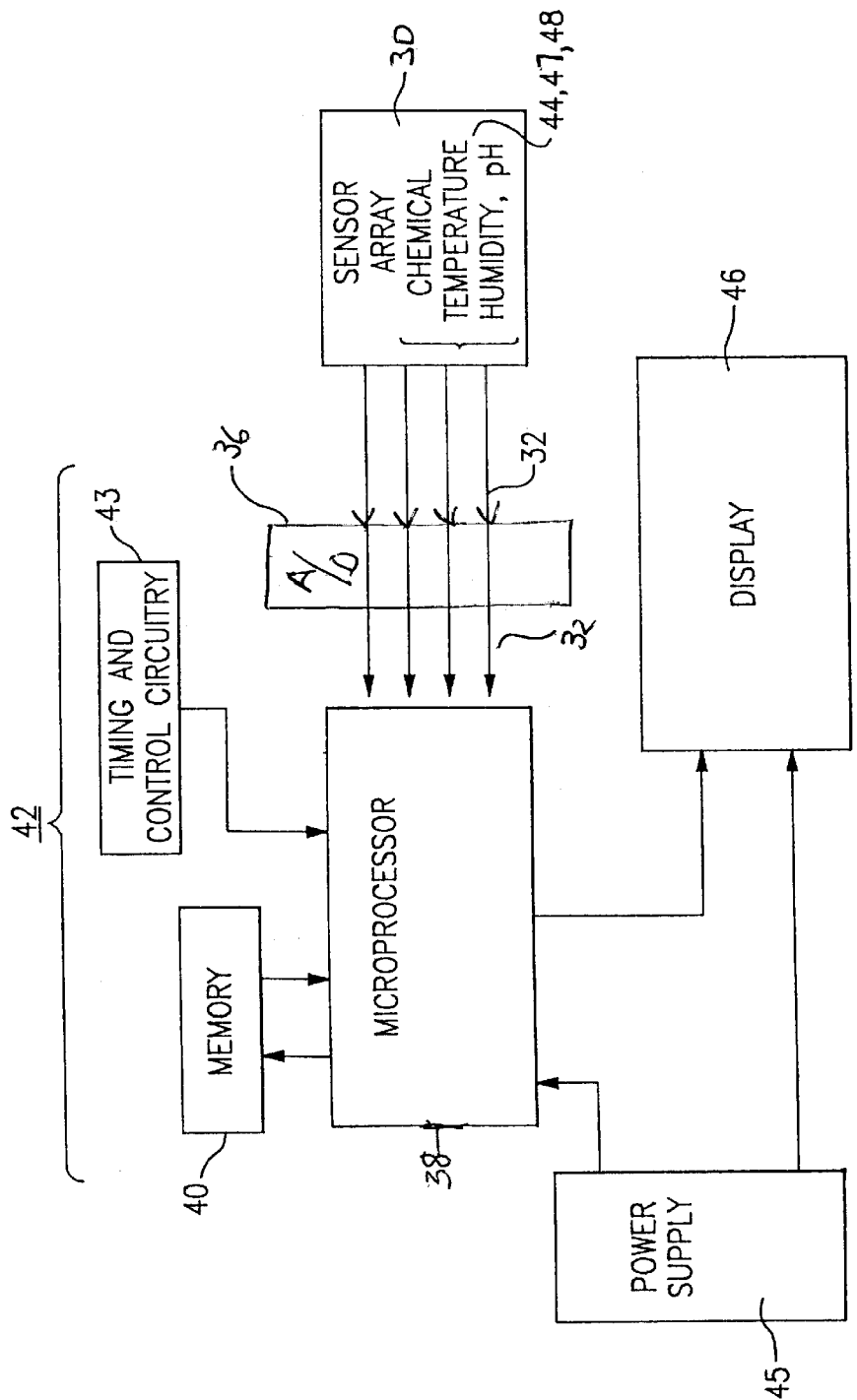
FIG. 2 is an electrical schematic diagram of the diagnostic device of FIG. 1.

Referring to FIGS. 1 and 2, a series of electrical traces 32 from each of the sensing elements of the array 30 are interconnected to provide an electrical path to a microprocessor 38, having suitable store memory 40, which according to this embodiment is also provided on the exterior surface 18 of the substrate 14. Preferably, the microprocessor 38 includes certain processing electronics 42 including an A/D converter 36 and timing and control circuitry 43 used in conjunction with a reference crystal (not shown) as is known. Batteries (not shown in FIG. 1) or other power supply 45 are electrically connected to each of the above components for powering the device 10. Each of the above convert an electrical signal generated from the sensing elements of the array 30 into a processed output signal. The storage memory 40 of the microprocessor 38 according to this embodiment includes a look-up table (not shown) which compares incoming signals to reference values in order to provide an analysis. The results are outputted to a compact LCD 46 provided on the exterior surface 18 of the elongated substrate 14. Alternately, an algorithm or other analytical means for providing a chemical analysis can be provided.

Still referring to FIGS. 1 and 2 and according to a typical procedure such as described in copending USSN 09/663, 698, the device 10 is inserted, for example, by placing the distal end 22 of the elongated substrate 14 directly into the mouth (not shown) of a patient, with the array 30 of chemical sensing elements being positioned in substantial immediate proximity with a target environment. This environment can include that contained within the mouth itself and also can include those vapors which are present in the esophagus, stomach, throat, ear, nose, sinus, colon, urinary tract, peritoneum, vagina, lungs, and an in vivo portion of the skin etc. As noted previously, each of the sensing elements of the array 30 are manufactured so as to produce an electrical change when at least one chemical component of a particular fluid is detected. The electrical changes are then transmitted along the traces 32 to the microprocessor 38 where the processing electronics 42 compares the transmitted electrical signals with those of the stored lookup table and then displays the results of those chemical components present in the target environment.

Due to the overall sensitivity of the miniature sensing elements of the array 30 utilized in this embodiment, at least one temperature sensor and/or humidity sensor and/or pH sensor 44, 47, 48, respectively, are also attached to the exterior surface 18 of the elongated substrate 14. Signals from each of the sensors 44, 47, 48 are also transmitted to the microprocessor 38 for processing thereof.

Figure 3:
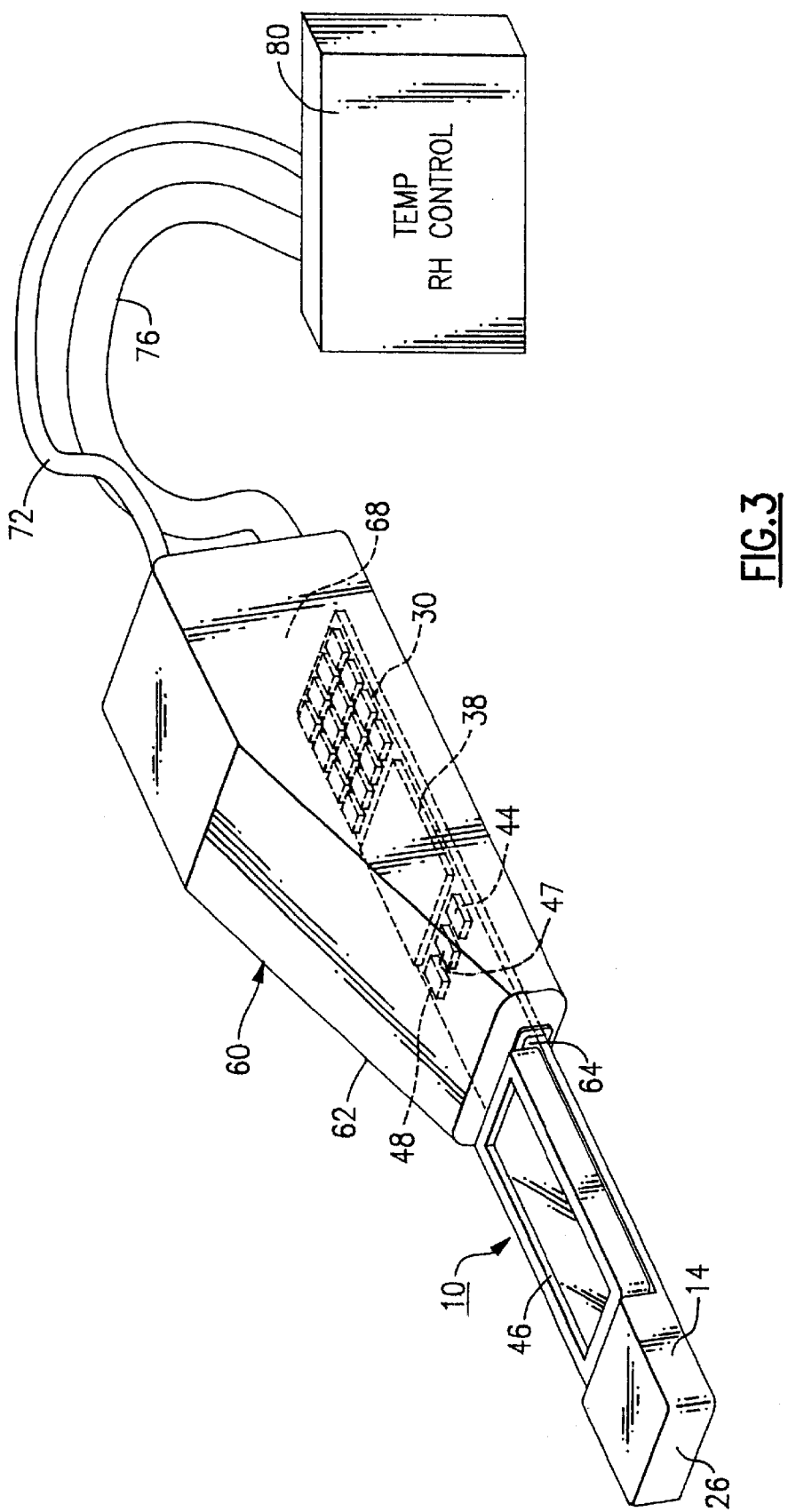
FIG. 3 is a sectional view of the diagnostic device of FIG. 1, including a conditioning sleeve in accordance with a first embodiment of the invention.

Referring to FIG. 3, there is shown a conditioning sleeve 60 made in accordance with a first preferred embodiment of the present invention and used with the described compact diagnostic device 10. The conditioning sleeve 60 is defined by a sleeve housing 62, made from tetrafluroethylene (teflon) or other suitable material which does not outgas or collect chemical components, and having a narrow input slot 64 that extends into an interior volume 68, the slot being sized to receive the distal end 22 of the elongated substrate 14. A pair of conduits 72, 76 fluidly interconnect the interior volume 68 with a temperature/relative humidity controller 80, which according to this embodiment provides warm moist air to the interior volume to replicate that of the intended target area (e.g., the mouth), which has a considerably higher temperature and relative humidity than ambient conditions. The controller 80 permits the temperature and relative humidity to be maintained specifically otherwise or in lieu of a control mechanism the temperature and humidity sensors 44, 47, of the device 10 can be utilized to monitor the conditions of the interior volume 68 until the temperature and humidity that the sensing element array 30 is exposed to approximates that of the intended target environment shown herein, though not specifically, it should be noted that the temperature/humidity controller 80 can also include a cooler element given that some conditioning of a sensing element array may involve acclimating the array to a cooler target environment.

Figure 4:
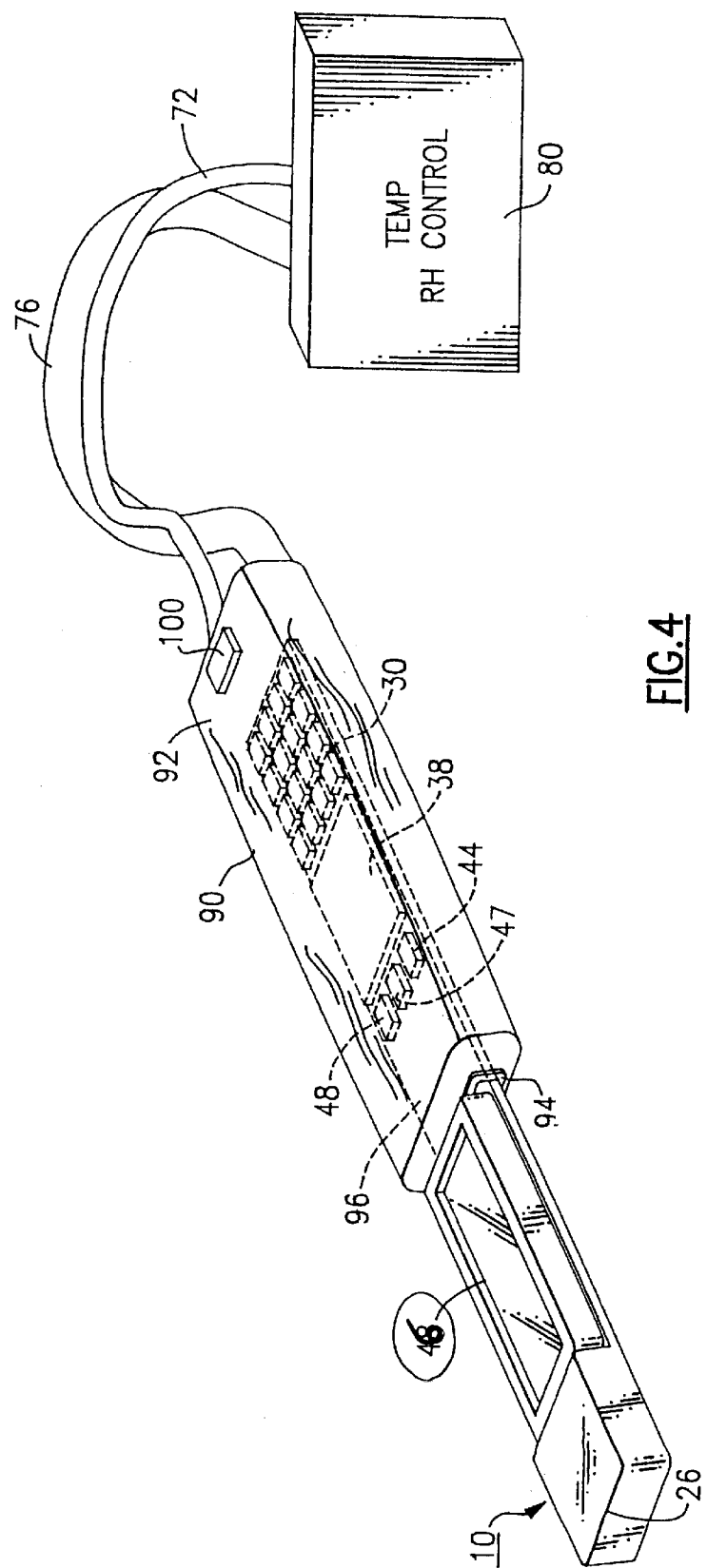
FIG. 4 is a perspective view of an electronic diagnostic device including a conditioning sleeve manufactured in accordance with a second embodiment of the present invention.

Referring to FIG. 4, a conditioning sleeve made in accordance with a second preferred embodiment is herein described. For the sake of clarity, similar part numbers are herein labeled with the same reference numerals. The sleeve 90 is also defined by a sleeve housing 92, made from tetrafluroethylene or other suitable material and having a narrow input slot 94 extending into an interior volume 96, the slot again being sized to receive the distal end 22 of the elongated substrate 14 of the device 10. In this instance, a heater element 100 is disposed within the interior volume 96 of the sleeve 90 wherein the sleeve is constructed to conform substantially to the shape of the substrate 14. Similarly, the sensors 44, 47 can be used to monitor the temperature and relative humidity of the interior volume 96 of the sleeve 90, or these environmental conditions can be controlled using the controller 80 through conduits 72,76.

PARTS LIST FOR FIGS. 1–4

10 diagnostic device
14 substrate
18 exterior surface
22 distal end
26 proximal end
30 sensing element array
32 electrical traces
36 A/D converter
38 microprocessor
40 storage memory
42 processing electronics
43 timing and control circuitry
44 temperature sensor
45 power supply
46 display
47 humidity sensor
48 pH sensor
60 conditioning sleeve
62 sleeve housing
64 input slot
68 interior volume
72 conduit
76 conduit
80 heater/humidity controller
90 conditioning sleeve
92 sleeve housing
94 input slot
96 interior volume
100 heating element

We claim:

1. Conditioning apparatus for a diagnostic instrument, said instrument comprising a substrate having at least one chemical sensing element capable of detecting at least one chemical component of a fluid indicative of a condition of a target and producing an electrical signal when said at least one chemical component of a fluid is detected, said conditioning apparatus including:
a sleeve sized for enclosing at least a portion of said substrate including said at least one chemical sensing element; and
means for producing environmental conditions within said sleeve which approximate those of an intended target to be used by said diagnostic instrument.

2. Conditioning apparatus as recited in claim 1, wherein said environmental conditions producing means includes means for at least one of heating and cooling the interior of said sleeve to at least one predetermined temperature.

3. Conditioning apparatus as recited in claim 1, wherein said environmental conditions producing means includes means for humidifying the interior of said sleeve to at least one predetermined relative humidity.

4. Conditioning apparatus as recited in claim 1, wherein said environmental conditions producing means includes at least one thermal conditioning element disposed within said sleeve.

5. Conditioning apparatus as recited in claim 1, wherein said intended target is a medical target.

6. Conditioning apparatus as recited in claim 1, wherein said intended target is an industrial target.

7. Conditioning apparatus as recited in claim 5, wherein said medical target is a body cavity including at least one of those in the group consisting of the mouth, ear, nose, urinary tract, peritoneum, vagina, and colon.

8. Conditioning apparatus as recited in claim 5, wherein said medical target is an in vivo portion of the skin of a patient.

9. Conditioning apparatus as recited in claim 5, wherein said medical target is the lungs.

10. A method of conditioning a diagnostic instrument, said instrument comprising a substrate having at least one disposed chemical sensing element, said method comprising the steps of:
placing a portion of said substrate including said at least one chemical sensing element into a sleeve;
conditioning said at least one chemical sensing element by providing an environment within the interior of said sleeve approximating that of an intended target;
removing said substrate from said sleeve; and
positioning said at least one chemical sensing element in substantial direct proximity with said intended target.

11. A method as recited in claim 10, wherein said conditioning step includes the steps of heating or cooling and humidifying the interior of said sleeve to condition said at least one chemical sensing element of said instrument from an ambient condition prior to using said instrument.

12. A method as recited in claim 11, wherein said intended target is a medical target.

13. A method as recited in claim 12, wherein said medical target is a body cavity selected from at least one of the group consisting of the ear, nose, sinus, mouth, urinary tract, peritoneum, vagina and colon.

14. A method as recited in claim 12, wherein said medical target is the lungs.

15. A method as recited in claim 12 wherein said medical target is an in vivo portion of the skin.

16. A method as recited in claim 10, wherein said intended target is an industrial area.

* * * * *